(12) United States Patent
Yomba Ngue

(10) Patent No.: US 10,016,477 B1
(45) Date of Patent: Jul. 10, 2018

(54) NATURAL COMPOSITION

(71) Applicant: Roger Yomba Ngue, Philadelphia, PA (US)

(72) Inventor: Roger Yomba Ngue, Philadelphia, PA (US)

(*) Notice: Subject to any disclaimer, the term of this patent is extended or adjusted under 35 U.S.C. 154(b) by 82 days.

(21) Appl. No.: 14/991,985

(22) Filed: Jan. 10, 2016

Related U.S. Application Data

(60) Provisional application No. 62/102,793, filed on Jan. 13, 2015.

(51) Int. Cl.
*A61K 36/67* (2006.01)
*A61K 36/00* (2006.01)
*A61K 36/906* (2006.01)
*A61K 36/9068* (2006.01)
*A61K 36/58* (2006.01)
*A61K 36/23* (2006.01)
*A61K 36/81* (2006.01)

(52) U.S. Cl.
CPC .......... *A61K 36/9068* (2013.01); *A61K 36/23* (2013.01); *A61K 36/58* (2013.01); *A61K 36/67* (2013.01); *A61K 36/81* (2013.01)

(58) Field of Classification Search
None
See application file for complete search history.

(56) References Cited

U.S. PATENT DOCUMENTS

| 6,444,237 | B1 | 9/2002 | Heleen |
| 7,128,932 | B2 | 10/2006 | Bombardelli et al. |
| 8,475,358 | B2 | 7/2013 | Scala |

OTHER PUBLICATIONS

Asante et al. (2009) Pharmacogn. J. vol. 1, Issue 3, pp. 201-206.*
Website document entitled: "Chicken Soup with Vegetables" (available at http://www.myjewishlearning.com/recipe/chicken-soup-with-vegetables/). downloaded Jul. 26, 2017.*
Ingabire et al. (2007) Planta Medica 73(09): P215.*
Malan et al. (2011) Afr. J. Reprod. Health 15[1]: 85-93.*

* cited by examiner

*Primary Examiner* — Christopher R Tate
*Assistant Examiner* — Russell G Fiebig
(74) *Attorney, Agent, or Firm* — RG Patent Consulting, LLC; Rachel Gilboy

(57) ABSTRACT

A medicinal compound includes ingredients combined in proportions substantially including: a portion of *Turraea Heterophylla*; a portion of Ginger; a portion of Carrot; providing a powdered portion of Celery; a portion of Parsley; and a portion of Pepper. The medicinal compound for both men and women has all natural ingredients designed to increase drive and stamina to provide consenting adults with a product that enhances their sensual activities without the side effects of pharmaceuticals.

1 Claim, 5 Drawing Sheets

NATURAL COMPOSITION

CROSS-REFERENCE TO RELATED APPLICATION

The present application is related to and claims priority from prior provisional application Ser. No. 62/102,793, filed Jan. 13, 2015 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of sexual enhancers and more specifically relates to a medicinal compound for both men and women, comprising all natural ingredients designed to increase drive and stamina to provide consenting adults with a product that enhances their sensual activities without the side effects of pharmaceuticals.

2. Description of the Related Art

Sex is a healthy and natural part of life. A physical expression of love, commitment or simple passion, a healthy sex life can be invigorating and meaningful. For most sexually active men and women, sex involves the conscious, positive expression of sexual energy in ways that enhance self-esteem, physical health, and an emotional relationship. Mutually beneficial and pleasurable, consensual sex is the cornerstone for most coupled relationships. Because sex can be so physically and emotionally gratifying, a healthy sex life is a key component of most coupled partnerships and a natural part of life for many single people, as well.

Various attempts have been made to solve problems found in sexual performance drugs art. Among these are found in: U.S. Pat. No. 8,475,358 to Jessica Scala; U.S. Pat. No. 7,128,932 to Ezio Bombardelli; U.S. Pat. No. 6,444,237 to Pamela A. Heleen. This prior art is representative of natural sexual performance herbs and supplements for increased libido in men and women.

None of the above inventions and patents, taken either singly or in combination, is seen to describe the invention as claimed.

Ideally, a medicinal compound should be user-friendly and safe in-use and, yet may operate reliably and be manufactured at a modest expense. Thus, a need exists for a to a medicinal compound for both men and women, comprising all natural ingredients designed to increase drive and stamina to provide consenting adults with a product that enhances their sensual activities without the side effects of pharmaceuticals and to avoid the above mentioned problems.

BRIEF SUMMARY OF THE INVENTION

In view of the foregoing disadvantages inherent in the known sexual enhancer art, the present invention provides a novel medicinal compound (Entitled The Natural Composition). The general purpose of the present invention, which will be described subsequently in greater detail, is to provide a medicinal compound for both men and women, comprising all natural ingredients designed to increase drive and stamina to provide consenting adults with a product that enhances their sensual activities without the side effects of pharmaceuticals.

A medicinal compound is disclosed herein comprising ingredients combined in proportions substantially including: a portion of *Turraea Heterophylla*; a portion of Ginger; a portion of Carrot; providing a powdered portion of Celery; a portion of Parsley; and a portion of Pepper.

The portion of Pepper is formed from a portion of Yellow Pepper and a portion of Black Pepper. The medicinal compound includes portions based on weight comprising 15 grams of *Turraea Heterophylla*; 7.5 grams of Ginger; 6.5 grams of Carrot; 4 grams of Celery; 4 grams of Parsley; 4.5 grams of Black Pepper; and 0.63 grams of Yellow Pepper. The medicinal compound includes portions based on percent are as follows: 35.6% *Turraea Heterophylla*; 17.8% Ginger; 15.4% Carrot; 9.5% Celery; 9.5% Parsley; 10.7% Black Pepper; and 1.5% Yellow Pepper. The compound may be formed as a powder. The powder may also be formed into a pill. The *Turraea Heterophylla* is Gouro Toothpick.

A method of forming a medicinal compound comprising the steps of: providing a powdered portion of *Turraea Heterophylla*; providing a powdered portion of Ginger; providing a powdered portion of Carrot; providing a powdered portion of Celer; providing a powdered portion of Parsley; and providing a powdered portion of Yellow Pepper; providing a powdered portion of Black Pepper; and blending the portions of *Turraea Heterophylla*, Ginger, Carrot, Celery Parsley, Yellow Pepper, and Black Pepper together to form the medicinal compound.

The powdered portions comprise: 15 grams of *Turraea Heterophylla*; 7.5 grams of Ginger; 6.5 grams of Carrot; 4 grams of Celery; 4 grams of Parsley; 4.5 grams of Black Pepper; and 0.63 grams of Yellow Pepper. The powdered portions are as follows: 35.6% *Turraea Heterophylla*; 17.8% Ginger; 15.4% Carrot; 9.5% Celery; 9.5% Parsley; 10.7% Black Pepper; and 1.5% Yellow Pepper. The medicinal compound is compressed and formed into a pill.

The present invention holds significant improvements and serves as a medicinal compound. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use

The various embodiments of the present invention will hereinafter be described in conjunction with the appended drawings, wherein like designations denote like elements

DETAILED DESCRIPTION

Figure 1:
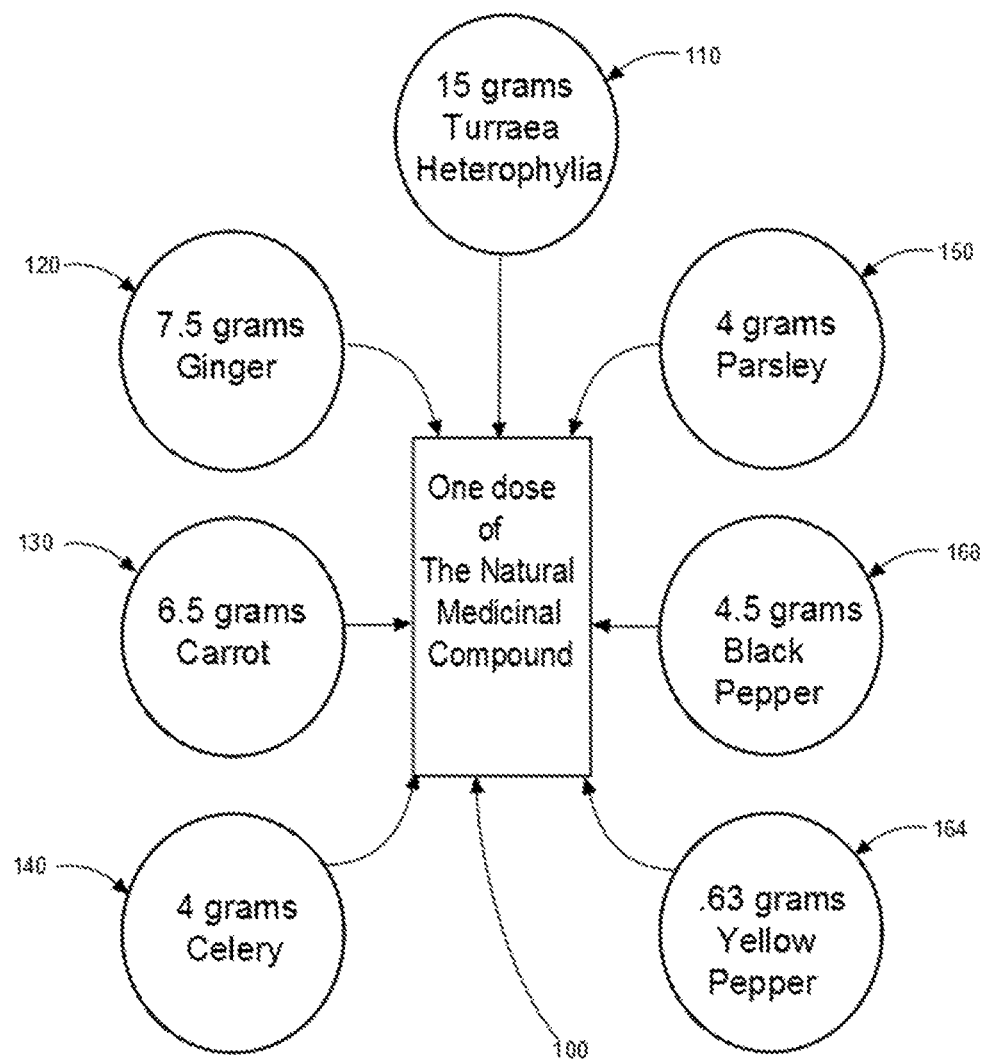
FIG. 1 is a flowchart illustrating portions based on weight of the medicinal compound according to an embodiment of the present invention
Figure 2:
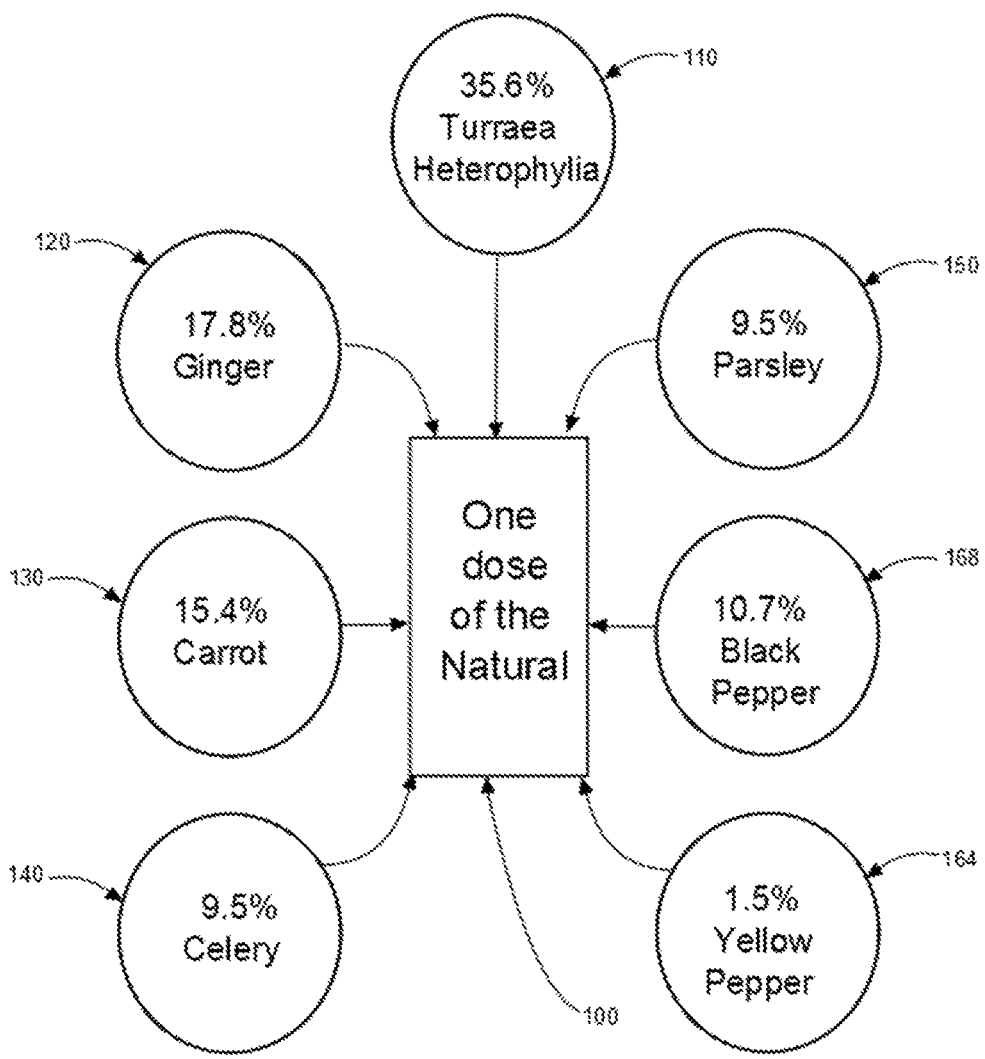
FIG. 2 is a flowchart illustrating portions based on percent of the medicinal compound according to an embodiment of the present invention
Figure 3:
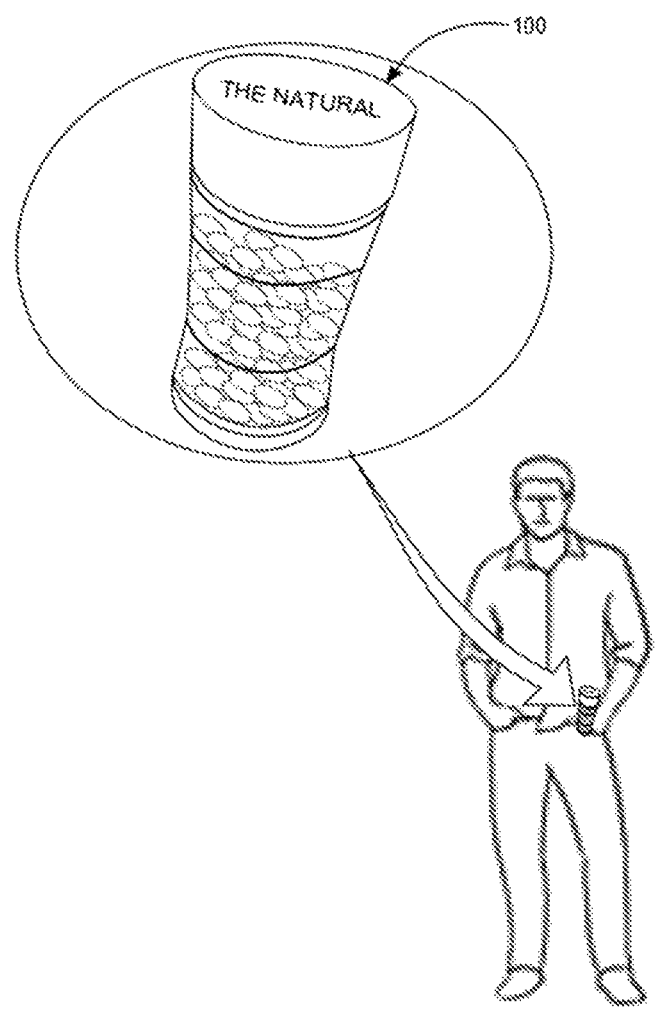
FIG. 3 shows a front perspective view illustrating a medicinal compound in an 'in-use' condition according to an embodiment of the present invention.

As discussed above, embodiments of the present invention relate to a sexual enhancer and more particularly to a medicinal compound (also referred to herein as The Natural Composition) for both men and women, comprising all natural ingredients designed to increase drive and stamina to provide consenting adults with a product that enhances their sensual activities without the side effects of pharmaceuticals.

Generally speaking, the Natural composition comprising a novel product offering consumers a practical solution to the aforementioned challenges. As the name implies, the Natural comprises a specially designed based on a formula used and perfected over one thousand years in his native Africa, is a blending of all-natural ingredients in pill form that is proven to improve sexual stamina for both men and women. The following ingredients would serve to infuse the Natural with optimal effectiveness:

- Mohne K'houly shrub/root (also known as the Gouro toothpick)
- Carrot
- Ginger rhizome
- Parsley
- Yellow pepper
- Black pepper
- Celery (leaves and stem)

The primary ingredient, a powdered concentrate of the Mohne K'houly (commonly referred to as the Gouro toothpick), is extracted from a plant indigenous to the Ivory Coast used in traditional African medicine for sexual dysfunction. The secondary ingredients listed above would also be rendered in powder form and blended with the Mohne K'houly to infuse the aphrodisiac with healthy vitamins and minerals that not only provide benefits to the body such as cancer prevention, body cleansing, blood pressure control, and bone strength, among many others, but also eliminate the need to use synthetic enhancers that can cause harmful side effects. It is recommended that the Natural formula be ingested three to four (3-4) hours before intercourse; as a result, one's natural libido would be heightened for a twenty-four (24) hour period. This increase in sexual desire and performance would be achieved safely, without the attendant headache, congestion, and heartburn (to name just a few examples) that typically result from pharmaceutical use.

Indeed, the Natural Composition is a cleverly designed sexual aide which would provide a simple and effective means of achieving optimal sexual pleasure. Used during a coupled partnership, the Natural would enable both men and women to enjoy the invigorating stimulation inherent in an all-natural tonic. Helping to add a new dimension of playfulness and fun to a partnership, the Natural could bring a sense of excitement and adventure back into the bedroom. A safe alternative to pharmaceuticals, the Natural would enable consumers to achieve sexual fulfillment without incurring potentially harmful detriments to physical health.

As this product is comprised completely of ingredients found in nature, the Natural could be safely combined with moderate alcohol consumption, which is not the case with virility drugs currently on the market. In addition, the ingredients that comprise the Natural would further health and happiness by helping curb maladies such as anxiety disorders, rheumatism, and high blood pressure while increasing brain activity.

The Natural Composition is an exciting product invention which would provide consumers with a tool that could readily improve their sex lives. Offering an exciting way in which to achieve optimal sexual pleasure, this product could prove a favorite of couples and singles alike. Affordably priced, the Natural Composition should be well received by sexually active consumers, a very sizable market potential.

Referring now to the drawings by numerals of reference there is shown in FIGS. 1-4B showing perspective views illustrating medicinal compound 100 according to an embodiment of the present invention.

Medicinal compound 100 is disclosed herein comprising ingredients combined in proportions substantially including: portion of *Turraea Heterophylla* 110; portion of Ginger 120; portion of Carrot 130; portion of Celery 140; portion of Parsley 150; and portion of Pepper 160. Portion of Pepper 160 is formed from a portion of Yellow Pepper 164 and portion of Black Pepper 168. *Turraea Heterophylla* 110 is Gouro Toothpick.

Figure 4A:
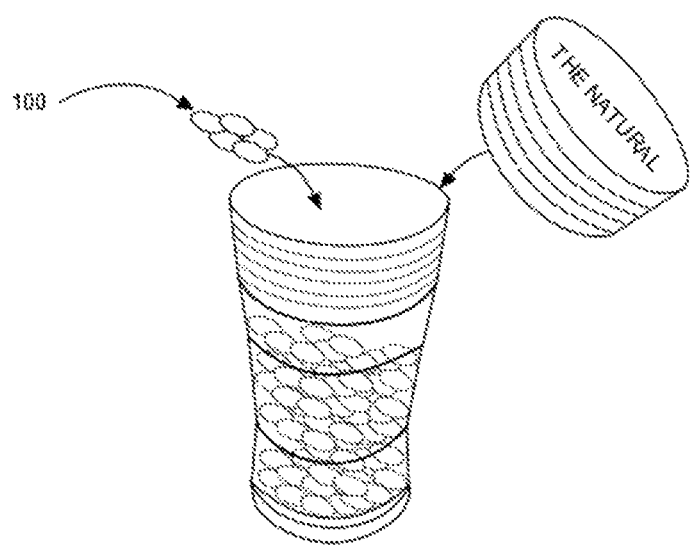
FIG. 4A shows a front perspective view illustrating the medicinal compound in powdered form according to an embodiment of the present invention.
Figure 4B:
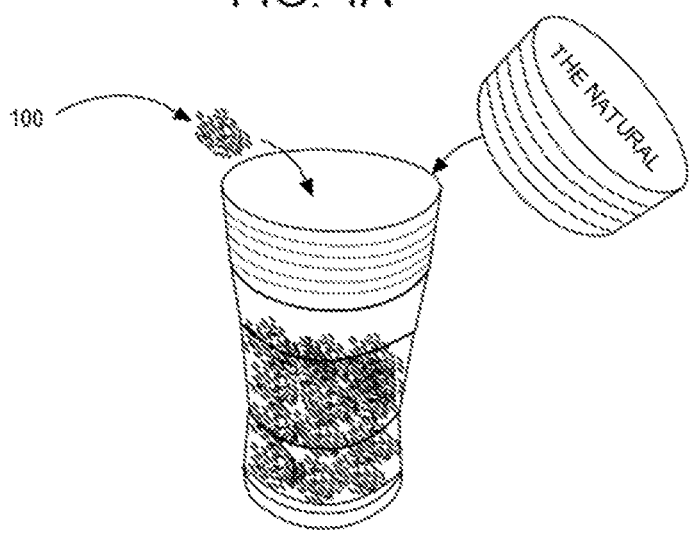
FIG. 4B shows a front perspective view illustrating the medicinal compound in pill form according to an embodiment of the present invention.

Medicinal compound 100 includes portions based on weight comprising 15 grams of *Turraea Heterophylla* 110; 7.5 grams of Ginger 120; 6.5 grams of Carrot 130; 4 grams of Celery 140; 4 grams of Parsley 150; 4.5 grams of Black Pepper 168; and 0.63 grams of Yellow Pepper 164. Medicinal compound 100 includes portions based on percent are as follows: 35.6% *Turraea Heterophylla* 110; 17.8% Ginger 120; 15.4% Carrot 130; 9.5% Celery 140; 9.5% Parsley 150; 10.7% Black Pepper 168; and 1.5% Yellow Pepper 164. Medicinal compound 100 may be formed as powder 400 as shown in FIG. 4A. Powder 400 may also be formed into pill 410 as shown in FIG. 4B.

The quantities given are for a preferred mixture but may be varied according to the desired potency and end product. The proportions given are relative to each other and if varying the total quantity of the finished product, one must be aware of the necessity to increase or decrease each ingredient proportionately.

Figure 5:
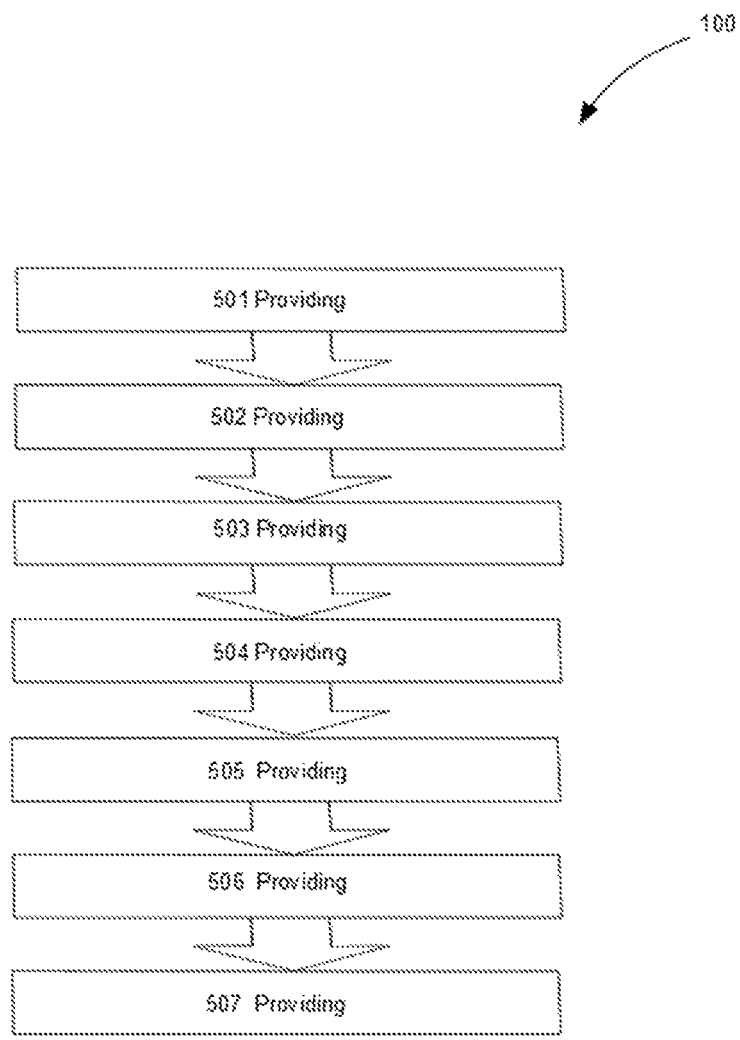
FIG. 5 is a flowchart illustrating a method of forming a medicinal compound according to an embodiment of the present invention.

Referring now to FIG. 5, showing flowchart 500 illustrating a method of forming medicinal compound 550 according to an embodiment of the present invention of FIGS. 1-4.

Method of forming medicinal compound 550 comprising the steps of: step one 501 providing powdered portion of *Turraea Heterophylla* 110; step two 502 providing powdered portion of Ginger 120; step three 503 providing powdered portion of Carrot 130; step four 504 providing powdered portion of Celery 140; step five 505 providing powdered portion of Parsley 150; step six 506 providing powdered portion of Yellow Pepper 164; step seven 507 providing powdered portion of Black Pepper 168; and step eight 508 blending portions of *Turraea Heterophylla* 110, Ginger 120, Carrot 130, Celery 140, Parsley 150, Yellow Pepper 164, and Black Pepper 168 together to form said medicinal compound.

It should be noted that the steps described in the method of use can be carried out in many different orders according to user preference. The use of "step of" should not be interpreted as "step for", in the claims herein and is not intended to invoke the provisions of 35 U.S.C. § 112, ¶6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. A medicinal composition for enhancement of sexual performance comprising an effective amounts of:

*Turraea Heterophylla*;
Ginger (*Zingiber officinale*);
Carrots (*Daucus carota*);
Celery (*Apium graveolens*);
Parsley (*Petroselinum crispum*); and
Pepper,
wherein said pepper is selected from a group of black peppercorns (*Piper nigrum*) and yellow bell peppers (*Capsicum annuum*);
wherein said composition is formed as a powder; and
wherein said powder is formed into a pill for digestion by a user.

* * * * *